United States Patent

Lock

[11] Patent Number: 5,171,505
[45] Date of Patent: Dec. 15, 1992

[54] PROCESS FOR SPINNING POLYPEPTIDE FIBERS

[75] Inventor: Robert L. Lock, Newark, Del.

[73] Assignee: E.I. du Pont de Nemours and Company, Wilmington, Del.

[21] Appl. No.: 618,505

[22] Filed: Nov. 28, 1990

[51] Int. Cl.$^5$ ............................................. D01F 4/00
[52] U.S. Cl. ................................. 264/202; 264/204; 264/210.8; 264/211.11; 264/211.16
[58] Field of Search ............... 264/184, 205, 210.8, 264/211.11, 202, 211.4, 211.16, 204

[56] References Cited

U.S. PATENT DOCUMENTS

| | | | |
|---|---|---|---|
| Re. 22,650 | 6/1945 | Bley | 106/141 |
| 2,697,085 | 12/1954 | Bamford et al. | 528/328 |
| 3,089,749 | 5/1963 | Ballard | 264/210.8 |
| 3,121,766 | 5/1962 | Ballard et al. | 264/202 |
| 3,696,058 | 10/1972 | Teti | 528/328 |
| 3,878,284 | 4/1975 | Schmitt | 264/205 |
| 3,988,411 | 10/1976 | Capozza | 264/205 |
| 4,029,727 | 6/1977 | Austin et al. | 264/202 |
| 4,062,921 | 12/1977 | Austin | 264/299 |
| 4,500,700 | 2/1985 | Urry | 528/328 |
| 4,594,409 | 6/1986 | Hayashi et al. | 528/328 |
| 4,857,403 | 8/1989 | Lucca et al. | 428/364 |

Primary Examiner—Leo B. Tentoni

[57] ABSTRACT

Polypeptide fibers, fiber spinnable solutions, and a process for forming polypeptide fibers are disclosed. The invention includes forming polypeptide fibers from spinning solutions containing a polypeptide, and a solvent selected from the group consisting of hexafluoroisopropanol, and a mixture of formic acid and at least one lithium halide.

17 Claims, No Drawings

PROCESS FOR SPINNING POLYPEPTIDE FIBERS

BACKGROUND OF THE INVENTION

1. Field of the Invention

The present invention relates to fiber spinnable polypeptide solutions and processes for forming polypeptide fibers. The invention also includes polypeptide fibers which may be produced from such processes. More particularly, the invention involves forming polypeptide fibers from spinning solutions comprising a polypeptide and a solvent selected from the group consisting of hexafluoroisopropanol, and a mixture of formic acid and at least one lithium halide.

2. Description of the Prior Art

Proteins are complex, high molecular weight polymers containing carbon, hydrogen, nitrogen, oxygen, and usually sulfur. These protein macromolecules, or polypeptides, are comprised of amino acid residues which are linked together by peptide bonds, (—CO—NH—). The 20 basic amino acids and their corresponding one-letter symbols are listed in Table I. Proteins which are found in nature have a wide range of properties depending on their particular amino acid sequence and generally fall into three categories: structural, regulatory, and catalytic. Certain naturally occurring structural polypeptides have fibrous structures including keratin, silk, elastin, and collagen. Structural polypeptides may also be synthesized by either recombinant DNA or, in some cases, by classical organic synthetic methods. Potential applications for structural polypeptide fibers include synthetic or simulated food, textiles, hard and soft tissue prostheses, artificial ligaments, and tough composite materials.

It is known in the art that fiber spinnable polypeptide solutions may be prepared by dissolving a polypeptide in strongly acidic solvents, such as trichloroacetic acid or trifluoroacetic acid. Organic solvents may also be used as in Ballard et al. U.S. Pat. No. 3,121,766, which discloses wet spinning polypeptide fibers from a birefringent solution of poly-gamma-methyl glutamate in mixed organic solvents such as methylene chloride/ethyl acetate. Acetone, ethyl acetate, or a mixture of these compounds were used as coagulating fluids.

Bamford and Hanby U.S. Pat. No. 2,697,085 discloses wet and dry spinning fibers from a solution containing anhydrocarboxy-amino-acids in a solvent comprising a major proportion of a monohydric phenol, a lower aliphatic carboxylic acid, a halogen-substituted lower aliphatic acid, or a mixture of these compounds. Hydroxyl-containing compounds such as water, methyl alcohol, and ethyl alcohol were used as coagulating fluids.

Bley U.S. Pat. No., RE 22,650 discloses preparing fiber spinnable polypeptide solutions containing a protein selected from the group consisting of silk fibroin, casein, gelatin, wool, and alginic acid in a solvent selected from quaternary benzyl-substituted ammonium bases.

Although the foregoing spinning solvents are commonly used, these solvents have the disadvantage of degrading the polypeptide in solution. Therefore, there is a need to prepare a fiber spinnable polypeptide solution containing a solvent which does not measurably degrade the polypeptide.

SUMMARY OF THE INVENTION

The present invention relates to a process for forming polypeptide fibers comprising forming a spinnable solution comprising 5% to 30% by weight of a polypeptide in a solvent selected from the group consisting of hexafluoroisopropanol, and a mixture of formic acid and at least one lithium halide. Preferably the solvent is selected from the group consisting of hexafluoroisopropanol, a mixture of formic acid and lithium chloride, and a mixture of formic acid and lithium bromide. It is desirable that the solutions be liquid crystalline and urea may be added to solutions containing hexafluoroisopropanol.

The solution is then extruded through a spinneret directly into a liquid coagulating medium; into an inert, non-coagulating fluid, and then into a liquid coagulating medium; or into an inert gas to remove the solvent. Preferably, the liquid coagulating medium is methanol. Preferably, the polypeptide is a synthetic polypeptide which consists essentially of multiple repetitive units of 5 to 150 amino acids, wherein each unit consists essentially of multiple repetitive sub-units of 3 to 30 amino acids, having sequences which confer some specific mechanical, chemical, or biological properties. The invention includes polypeptide fibers which may be prepared from such processes which include at least one of the following repetitive units or sub-units:

SGLDFDNNALRIKLG,

LSVQTSAPLTVSDGK,

GAGAGS,

GVGVP,

VPGVG, and

RGD.

The invention also includes fiber spinnable solutions comprising 5% to 30% by weight of a polypeptide in either hexafluoroisopropanol, or a mixture of formic acid and at least one lithium halide.

DETAILED DESCRIPTION OF THE INVENTION

The polypeptides of the present invention may be naturally occurring or synthesized by techniques known in the art. In some instances, it is desirable that the polypeptides be capable of forming cross beta-sheet structures. Examples of polypeptides capable of forming cross beta-sheet structures are:

MASMTGLLG-(SGLDFDNNALRIKLG)26-SGLL and

MASMTG-(LSVQTSAPLTVSDGK)14-LL.

The term, cross beta-sheet structure is used to refer to the structure which results when a polypeptide chain, as a consequence of specific features of its amino acid sequence, spontaneously folds back and forth on itself in a regular way to form a long, narrow molecular ribbon held together by hydrogen bonds between the amide groups of the polypeptide backbone. Such cross beta-sheet structures can be constructed so that under certain conditions, they spontaneously associate into aggregates composed of multiple, aligned copies of the structure and form stiff microfibrils. Solutions of these stiff microfibrils can form lyotropic liquid crystalline phases which can be spun to form strong fibers.

The synthetic polypeptides of the present invention may consist essentially of multiple repetitive units of 5 to 150 amino acids, wherein each unit consists essentially of multiple repetitive sub-units of 3 to 30 amino acids, having sequences which confer some specific mechanical, chemical, or biological properties.

Suitable synthetic polypeptides include, for example, those polypeptides having one of the following repetitive units:

SGLDFDNNALRIKLG,

LSVQTSAPLTVSDGK,

GAGAGS, (GVGVP)$_8$ (GAGAGS)$_8$, (VPGVG)$_4$ VAAGY (GAGAGS)$_9$ GAA, and (GAGAGS)$_9$ GAAVTGRGDSPASAAGY.

Suitable natural polypeptides include, for example, silk fibroin, casein, gelatin, and collagen. Preferably, the synthetic or natural polypeptide has a calculated molecular weight from 20,000 to 80,000 and more preferably from 80,000 to 350,000. By the term, calculated molecular weight, it is meant the molecular weight based on the true molecular formula of the subject polypeptide. By the term, apparent molecular weight, it is meant the molecular weight of the subject polypeptide based on standard analytical techniques such as gel electrophoresis, or gel permeation chromatography. Different techniques for deriving or synthesizing polypeptides are known in the art. For example, selected polypeptides may be derived from natural sources such as silk cocoons. To a more limited extent, polypeptides may also be synthesized using classical organic synthesis methods described in Kirk-*Othmer Encyclopedia of Chemical Technolology*, Vol. 18, 3rd edition, pp. 888-911. Recombinant DNA methods as described in Watson & Tooze, *Recombinant DNA—A Short Course*, 1983, are also useful in preparing structural proteins.

The fiber spinnable solution is then prepared by dissolving the polypeptide in a solvent selected from the group consisting of hexafluoroisopropanol, and a mixture of formic acid and at least one lithium halide, such that the solution contains 5% to 30% by weight of the polypeptide. Preferably, the solvent is selected from the group consisting of hexafluoroisopropanol, a mixture of formic acid and lithium chloride, and a mixture of formic acid and lithium bromide. More preferably, a polypeptide/hexafluoroisopropanol solution is prepared, because there is no measurable degradation of the polypeptide if this solvent is used. In contrast, if a polypeptide/formic acid/lithium chloride or lithium bromide solution is prepared, there is slight degradation of the polypeptide. Signs of polypeptide degradation include change of color and loss of solution viscosity. Both spinnable solutions are prepared at room temperature. However, solutions containing the solvent, hexafluoroisopropanol, may be safely heated at a temperature up to about 30° C. for several hours to dissolve the polypeptide more rapidly without any measurable degradation, while the solution containing the mixed solvent of formic acid and lithium chloride or formic acid and lithium bromide should not be heated. The mixed solvent should contain 5% to 15% by weight of lithium chloride or lithium bromide and 85% to 95% by weight of formic acid and may be cooled to about 10° C. to prevent further degradation of the polypeptide. It has been found that while certain polypeptides are not sufficiently soluble in formic acid to yield spinnable solutions, the addition of 5% to 15% by weight of lithium chloride or lithium bromide increases the polypeptide solubility sufficiently to form spinnable solutions. For polypeptide/hexafluoroisopropanol solutions, 0.5% to 25% by weight of urea may be added to enhance processibility. It is believed that urea is an effective additive, because it helps to break the hydrogen bonds which hold the peptide chains together.

The spinnable solution may then be spun into fibers using elements of processes known in the art. These processes include, for example, wet spinning, dry-jet wet spinning, and dry spinning.

In a wet spinning process, the spinning solution is extruded directly into a coagulating bath. The coagulant may be any fluid wherein the hexafluoroisopropanol, or mixture of formic acid and lithium chloride or formic acid and lithium bromide is soluble, but wherein the polypeptide is insoluble. Examples of suitable coagulating fluids include water, methanol, ethanol, isopropyl alcohol, and acetone. Methanol has been found to be the preferred coagulating fluid for most polypeptide spinning solutions. In certain instances, the resulting fibers may be dried and subsequently hot drawn to improve their tensile properties. If the fibers are not amenable to hot drawing, the fibers may be cold drawn while still wet with coagulating fluid. Preferably, the fibers are dried under tension in order to prevent shrinkage and to obtain improved tensile properties.

In a dry-jet wet spinning process, the spinning solution is attenuated and stretched in an inert, non-coagulating fluid, e.g., air, before entering the coagulating bath. For liquid crystalline spinning solutions, this stretching causes an alignment of the molecules which are then frozen in an oriented arrangement in the coagulation bath. As a result, the fibers often have improved tensile properties over wet-spun fibers. Suitable coagulating fluids are the same as those used in a wet spinning process.

In a dry spinning process, the spinning solution is not spun into a coagulating bath. Rather, the fibers are formed by evaporating the solvent into an inert gas which may be heated.

TESTING METHODS

Physical properties such as tenacity, elongation, and initial modulus were measured using methods and instruments which conformed to ASTM Standard D 2101-82, except that the test specimen length was one inch. Reported results are for individual filaments.

In the following examples, parts and percentages are by weights, unless otherwise indicated.

EXAMPLE 1

A 7.5% solution of a polypeptide having the amino acid sequence, MASMTGLLG (SGLDFDNNALRIKLG)$_{26}$ SGLL, with a calculated molecular weight of approximately 42,000 and 2.2% urea in the solvent, hexafluoroisopropanol, hereinafter HFIP, was prepared by adding the solvent to the dry ingredients in a heat-sealed polyethylene packet, mixing the solution thoroughly by hand-kneading the packet and allowing the mixture to stand overnight at room temperature. The solution showed a translucent, opalescent appearance and yield-stress rheology which is characteristic of liquid crystalline solutions. A sample of the solution was placed between crossed polarizing filters which were set apart at 90 degrees in the optical train of a light microscope. The sample was examined in the resulting dark field and found to be strongly birefringent, showing zones which brightened and darkened as the sample was rotated in the plane of the microscope stage. The solution was characterized as liquid crystalline on the basis of its rheology, overall appearance, and optical properties.

The solution was then filtered through a stainless steel screen pack consisting, in order, of 50, 325, and 50 mesh screens prior to loading into a syringe for wet spinning. The syringe was capped and centrifuged to disengage any air bubbles trapped in the solution. A syringe pump was then used to force the solution out of the syringe through a 0.005 inch (0.013 cm) diameter×0.010 inch (0.025 cm) length orifice in a stainless steel spinneret and directly into a container of acetone at room temperature. The syringe pump speed was set to deliver the solution at 0.0034 ml/min. The filament which formed as the solution was extruded into the acetone was allowed to fall freely and to coil on itself at the bottom of the container. After at least 10 minutes of coagulation in the acetone, the filament was removed and allowed to dry in air at room temperature to produce an 18 denier (20 dtex) fiber having a tenacity of 0.4 gpd (0.35 dN/tex), an elongation of 34%, and an initial modulus of 16 gpd (14 dN/tex).

Alternatively, the wet filament was drawn to 2×its original length as it was removed from the acetone. Wet drawing the filament to 1.5×its original length followed by air drying produced a 5 denier (5.6 dtex) fiber having a tenacity of 1.5 gpd (1.3 dN/tex), an elongation of 16%, and an initial modulus of 45 gpd (40 dN/tex).

In a separate experiment, a dried filament was drawn to 2 to 3×its original length while passing over a 200° C. hot pin to produce a 5 denier (5.6 dtex) fiber having a tenacity of 2.6 gpd (2.3 dN/tex), an elongation of 15%, and an initial modulus of 44 gpd (39 dN/tex).

EXAMPLE 2

A solution containing 11.9% of the polypeptide used in EXAMPLE 1, and 4.0% urea in the solvent, HFIP, was prepared by adding the solvent to the dry polypeptide in a heat-sealed polyethylene packet, mixing thoroughly, and allowing the mixture to stand for 5 days with additional intermittent, vigorous mixing. The thick solution had a translucent, opalescent appearance and yield-stress rheology which is characteristic of liquid crystalline solutions. The solution was characterized as liquid crystalline on the basis of its rheology, overall appearance, and optical properties.

The solution was then transferred to a syringe fitted with a stainless steel screen pack consisting, in order, of 50, 325, 325, and 50 mesh screens. The syringe was capped and centrifuged to disengage air bubbles trapped in the solution. A syringe pump was then used to force the solution through the screen pack and out of the syringe through a 0.005 inch (0.013 cm) diameter×0.010 inch (0.025 cm) length orifice in a stainless steel spinneret. The syringe pump speed was set to deliver solution at 0.068 ml/min. The syringe pump, syringe, and spinneret were arranged such that the stream of solution emerging from the orifice passed through a 0.5 inch (1.27 cm) air gap and into a pan of acetone at room temperature. Filaments were produced by the coagulation of the spinning solution in the acetone and were collected at a rate of 12 ft./min. (3.66 m/min.) by winding onto bobbins on a motor-driven windup and allowed to dry in air at room temperature.

After drying in air at room temperature, the filament was removed from the bobbins and the fiber was found to be 15.6 denier (17.3 dtex) with a tenacity of 1.2 gpd (1.1 dN/tex), elongation of 9%, and an initial modulus of 58 gpd (51 dN/tex).

EXAMPLE 3

The polypeptide solution used in Example 2 was spun in a dry-spinning process. The syringe pump, syringe, and spinneret were arranged such that the stream of solution emerging from the orifice passed through an approximately 18 inch (45.7 cm) air-gap, wherein air flowing at room temperature evaporated the HFIP. The syringe pump speed was set to deliver solution at 0.0068 ml/min. The partially dried filament at the bottom of the air-gap was wound onto metal mesh bobbins and allowed to dry completely in air at room temperature. The dried fiber was 24 denier (27 dtex) having a tenacity of 0.1 gpd (0.09 dN/tex), elongation of 37%, and an initial modulus of 1.5 gpd (1.3 dN/tex).

EXAMPLE 4

A 19.5% solution of a polypeptide having the amino acid sequence, MASMTG (LSVQTSAPLTVSDGK)$_{14}$ LL with a calculated molecular weight of approximately 21,500 in the solvent, HFIP, was prepared by adding the solvent to the dry polypeptide in a heat-sealed polyethylene packet, mixing thoroughly, and allowing the mixture to stand for 4 days with additional intermittent, vigorous mixing. The resulting solution had a translucent, opalescent appearance and yield-stress rheology which is characteristic of liquid crystalline solutions. A sample of the solution was placed between crossed polarizing filters which were set apart at 90 degrees in the optical train of a light microscope. The sample was examined in the resulting dark field and found to be birefringent, showing zones which brightened and darkened as the sample was rotated in the plane of the microscope stage. The solution was characterized as liquid crystalline on the basis of its rheology, overall appearance, and optical properties.

The solution was then transferred to a syringe fitted with a stainless steel screen pack consisting, in order, of 50, 325, 325, and 50 mesh screens. The syringe was capped and centrifuged to disengage air bubbles trapped in the solution. A syringe pump was then used to force the solution through the screen pack and out of the syringe through a 0.005 inch (0.013 cm) diameter×0.010 inch (0.025 cm) length orifice in a stainless steel spinneret and directly into a container of methanol at room temperature. The syringe pump speed was set to deliver solution at 0.0034 ml/min. The white, opaque filament which formed as the solution was extruded into the methanol was allowed to fall freely and to coil on itself at the bottom of the container.

After at least 1 hour of coagulation in the methanol, the filament was removed and allowed to dry in air at room temperature to produce an 80 denier (90 dtex) fiber having a tenacity of 0.30 gpd (0.26 dN/tex), an elongation of 2%, and an initial modulus of 15.5 gpd (13.7 dN/tex).

Alternatively, after 1 hour of coagulation in methanol, the filament was drawn to 2.5×its original length while still immersed in methanol and was then allowed to dry in air at room temperature to produce a 44 denier (50 dtex) fiber having a tenacity of 0.4 gpd (0.35 dN/tex), an elongation of 2.5%, and an initial modulus of 20 gpd (17.7 dN/tex).

EXAMPLE 5

A 14.1% solution of a polypeptide having the amino acid sequence, fMDPVVLQRRDWENPGVTQLNRLAAHPPFASDPMGAGS
[(GAGAGS)$_6$]$_{28}$(GAGAGS)$_5$
GAGAMDPGRYQLSAGRYHYQLVWCQK, with an apparent molecular weight of 150,000 and a calculated molecular weight of 76,000 in HFIP was prepared by adding the solvent to the dry polypeptide in a heat-sealed plastic packet, mixing thoroughly, and allowing the mixture to stand for 14 days with additional intermittent, vigorous mixing. The solution was thick, but free-flowing, opaque, and light grayish-tan in color.

The solution was then transferred to a syringe fitted with a stainless steel screen pack consisting, in order, of 50, 325, 325, and 50 mesh screens. The syringe was capped and centrifuged to disengage any air bubbles trapped in the solution. A syringe pump was then used to force the solution through the screen pack and out of the syringe through a 0.005 inch (0.013 cm) diameter×0.010 inch (0.025 cm) length orifice in a stainless steel spinneret and directly into a container of methanol at room temperature. The syringe pump speed was set to deliver solution at 0.0034 ml/min. The filament which formed as the solution was extruded into the methanol was allowed to fall freely and to coil on itself at the bottom of the container.

After 30 to 180 minutes of coagulation in methanol, the filament was removed and allowed to dry in air at room temperature to produce a 96 denier (106 dtex) fiber having a tenacity of 0.5 gpd (0.44 dN/tex), an elongation of 2.1%, and an initial modulus of 33.4 gpd (29.5 dN/tex).

Alternatively, the fiber properties were improved by drawing the still-wet filament to 3×its original length before drying in air at room temperature. The wet drawing produced a 34 denier (37 dtex) fiber having a tenacity of 1.9 gpd (1.68 dN/tex), an elongation of 26%, and an initial modulus of 55 gpd (48.6 dN/tex).

EXAMPLE 6

An 18.1% solution of a polypeptide having the amino acid sequence, fMDPVVLQRRDWENPGVTQLNRLAAHPPFASDPMGAGS
(GAGAGS)$_2$[(GVGVP)$_8$ (GAGAGS)$_8$]$_{12}$
(GVGVP)$_8$ (GAGAGS)$_5$
GAGAMDPGRYQLSAGRYHYQLVWCQK, with an apparent molecular weight of 94,000 and a calculated molecular weight of 84,000 in HFIP was prepared by adding the solvent to the dry polypeptide in a heat-sealed plastic packet, mixing thoroughly, and allowing the mixture to stand overnight with intermittent, vigorous mixing at room temperature. The solution was thick, opaque, and greenish-yellow in color.

The solution was then filtered through a stainless steel screen pack consisting, in order, of 50, 325, and 50 mesh screens prior to loading into a syringe for wet spinning. A syringe pump was used to force the solution out of the syringe through a 0.003 inch (0.008 cm) diameter×0.006 inch (0.015 cm) length orifice in a stainless steel spinneret and directly into a container of methanol at room temperature. The syringe pump was set to deliver solution at 0.0034 ml/min. The filament which formed as the solution was extruded into the methanol was allowed to fall freely and to coil on itself at the bottom of the container.

After at least 10 minutes of coagulation, the filament was transferred to a pan of methanol and was then drawn to 6×its original length. The ends of the drawn filament were held fixed in order to prevent shrinkage, while the filament was dried in air at room temperature to produce a 5 denier (5.6 dtex) fiber having a tenacity of 3 gpd (2.6 dN/tex), an elongation of 11%, and an initial modulus of 73 gpd (64.5 dN/tex).

EXAMPLE 7

An 18.1% solution of a polypeptide having the amino acid sequence, fMDPVVLQRRDWENPGVTQLNRLAAHPPFASDPMGAGS
(GAGAGS)$_6$ GAA[(VPGVG)$_4$ VAAGY (GAGAGS)$_9$GAA]$_{13}$
(VPGVG)$_4$ VAAGY
(GAGAGS)$_2$GAGAMDPGRYQLSAGRYHYQLVWCQK, with an apparent molecular weight of 97,000 and a calculated molecular weight of 89,000 in HFIP was prepared by adding the solvent to the dry polypeptide in a heat-sealed plastic packet, mixing thoroughly, and allowing the mixture to stand for six days with intermittent, vigorous mixing at room temperature. The solution was thin, free-flowing, slightly cloudy, and pale yellow in color.

The solution was then filtered through a stainless steel screen pack consisting, in order, of 50, 325, and 50 mesh screens prior to loading into a syringe for wet spinning. The syringe was capped and centrifuged to disengage any air bubbles trapped in the solution. A syringe pump was then used to force the solution out of the syringe through a 0.005 inch (0.013 cm) diameter×0.010 inch (0.025 cm) length orifice in a stainless steel spinneret and directly into a container of methanol at room temperature. The syringe pump speed was set to deliver solution at 0.034 ml/min. The filament which formed as the solution was extruded into the methanol was allowed to fall freely and to coil on itself at the bottom of the container.

After at least 10 minutes of coagulation in methanol, the filament was transferred to a pan of methanol and was then drawn to 4×its original length. The ends of the drawn filament were held fixed in order to prevent shrinkage, while the filament was dried in air at room temperature to produce a 36 denier (40 dtex) fiber having a tenacity of 2 gpd (1.8 dN/tex), an elongation of 8%, and an initial modulus of 62 gpd (54.7 dN/tex).

Alternatively, if ends of the drawn filament were not held fixed and the filament was allowed to shrink during air drying at room temperature, a 48 denier (53 dtex) fiber having a tenacity of 1.3 gpd (1.1 dN/tex), an elongation of 45%, and an initial modulus of 57 gpd (50.3 dN/tex) was produced.

EXAMPLE 8

An 18.65% solution of a polypeptide having the amino acid sequence, fMDPVVLQRRDWENPGVTQLNRLAAHPPFASDPMGAGS
(GAGAGS)$_6$ GAAVTGRGDSPASAAGY
[(GAGAGS)$_9$ GAAVTGRGDSPASAAGY]$_{12}$
(GAGAGS)$_2$ GAGAMDPGRYQLSAGRYHYQLVWCQK, with an apparent molecular weight of 110,000 and a calculated molecular wt. of 73,000 in HFIP was prepared by adding the solvent to the dry polypeptide in a heat-sealed plastic packet, mixing thoroughly, and allowing the mixture to stand overnight with intermittent, vigorous mixing at room temperature. The solution was thin, free-flowing, translucent, and off-white in color.

The solution was then filtered through a stainless steel screen pack consisting, in order, of 50, 325, and 50 mesh screens prior to loading into a syringe for wet spinning. A syringe pump was used to force the solution out of the syringe through a 0.005 inch diameter × 0.010 inch length orifice in a stainless steel spinneret and directly into a container of methanol at room temperature. The syringe pump speed was set to deliver solution at 0.034 ml/min. The filament which formed as the solution was extruded into the methanol was allowed to fall freely and to coil on itself at the bottom of the container.

After at least 10 minutes of coagulation in methanol, the filament was transferred to a pan of methanol and was then drawn to 4× its original length. The ends of the drawn filament were held fixed in order to prevent shrinkage while the filament was dried in air at room temperature to produce a 29 denier (32 dtex) fiber having a tenacity of 1.8 gpd (1.6 dN/tex), an elongation of 19%, and an initial modulus of 65 gpd (57 dN/tex).

Alternatively, if the ends of the filament were not fixed and the filament was allowed to shrink during air drying at room temperature, a 31 denier (34 dtex) fiber having a tenacity of 1.7 gpd (1.5 dN/tex), an elongation of 40%, and an initial modulus of 52 gpd (46 dN/tex) was produced.

If the extruded filament was removed from the methanol and air dried at room temperature without drawing, a 95 (105 dtex) denier fiber having a tenacity of 0.53 gpd (0.47 dN/tex), an elongation of 2.1%, and an initial modulus of 31 gpd (27.4 dN/tex) was produced.

EXAMPLE 9

An 18.3% solution of the polypeptide used in Example 6 in HFIP was prepared by adding the solvent to the dry polypeptide in a heat-sealed plastic packet, mixing thoroughly, and allowing the mixture to stand overnight with intermittent, vigorous mixing at room temperature. The solution was thick, but free-flowing, nearly clear, and yellowish green in color.

The solution was then filtered through a stainless steel screen pack consisting, in order, of 50, 325, and 50 mesh screens prior to loading into a syringe for wet spinning. A syringe pump was used to force the solution out of the syringe through a 0.005 inch (0.013 cm) diameter × 0.010 inch (0.025 cm) length orifice in a stainless steel spinneret into a beaker of methanol at room temperature. The syringe pump speed was set to deliver solution at 0.034 ml/min. The syringe pump, syringe, and spinneret were arranged such that the stream of solution emerging from the orifice passed through a 0.25 inch (0.64 cm) air-gap into a pan of methanol at room temperature. The filament which formed by the coagulation of the solution in the methanol was collected by winding it onto bobbins on a motor-driven wind-up. Varying degrees of tension were applied to the filament during spinning by varying the collection rate from 8 to 14 fpm (2.4 to 4.3 m/min). The filament was thus drawn to 1.6× its original length during spinning, based on a nominal velocity of 8.8 fpm (2.4 m/min) for the solution exiting through the 0.005 inch (0.013 cm) orifice. Although the filament remained in the methanol coagulating bath for less than 30 seconds, it was kept wet by soaking the bobbins on the wind-up with methanol from a wash bottle.

After the filament was soaked overnight in fresh methanol, it was collected at a rate of 8 fpm (2.4 m/min) onto a bobbin, removed, and drawn to 2× its original length while still wet with methanol. Subsequent air drying produced a 6.3 denier (6.9 dtex) fiber having a tenacity of 1.2 gpd (1.1 dN/tex), an elongation of 17%, and an initial modulus of 33 gpd (29 dN/tex).

EXAMPLE 10

A 28.1% solution of the polypeptide used in Example 5 in a solvent mixture of 90% formic acid and 10% lithium chloride was prepared by adding the mixed solvent to the dry polypeptide in a heat-sealed plastic packet, mixing thoroughly, and allowing the mixture to stand overnight at room temperature. The solution was thick, but free-flowing, clear, and amber in color.

The solution was then filtered through a stainless steel screen pack consisting, in order, of 50, 325, and 50 mesh screens prior to loading into a syringe for wet spinning. A syringe pump was used to force the solution out of the syringe through a 0.005 inch (0.013 cm) diameter × 0.010 inch (0.025 cm) length orifice in a stainless steel spinneret and directly into a container of methanol at room temperature. The syringe pump speed was set to deliver solution at 0.0034 ml/min. The filament which formed as the solution was extruded into the methanol was allowed to fall freely and to coil on itself at the bottom of the container.

After at least 10 minutes of coagulation in methanol, the filament was transferred to a pan of methanol and was then drawn to 2.5× its original length. The ends of the drawn filament were held fixed in order to prevent shrinkage while the filament was dried in air at room temperature to produce a 42 denier (46 dtex) fiber having a tenacity of 1.0 gpd (0.883 dN/tex), an elongation of 13%, and an initial modulus of 40 gpd (35.3 dN/tex).

EXAMPLE 11

A 32.7% solution of the polypeptide used in Example 6 in a solvent mixture of 90% formic acid and 10% lithium chloride was prepared by adding the mixed solvent to the dry polypeptide in a heat-sealed plastic packet, mixing thoroughly, and allowing the mixture to stand overnight at room temperature. The solution was thick, but free-flowing, clear, and golden brown in color.

The solution was then filtered through a stainless steel screen pack consisting, in order, of 50, 325, and 50 mesh screens prior to loading into a syringe for wet spinning. A syringe pump was used to force the solution out of the syringe through a 0.005 inch (0.013 cm) diameter × 0.010 inch (0.025 cm) length orifice in a stainless steel spinneret directly into a container of methanol at room temperature. The syringe pump was set to deliver solution at 0.034 ml/min. The filament which formed as the solution was extruded into the methanol was allowed to fall freely and to coil on itself at the bottom of the container.

After soaking overnight in a pan of methanol, the extruded filament was drawn to 4×its original length. The ends of the drawn filament were held fixed in order to prevent shrinkage while the filament was dried in air at room temperature to produce a 38 denier (42 dtex) fiber having a tenacity of 1.0 Egq0688pd (0.883 dN/tex), an elongation of 16% and an initial modulus of 47 gpd (41.9 dN/tex).

EXAMPLE 12

A 7.4% solution of the polypeptide used in Example 1 in the solvent, HFIP, was prepared by adding the solvent to the dry polypeptide in a heat-sealed polyethylene packet, mixing thoroughly, and allowing the mixture to stand overnight at room temperature with additional intermittent, vigorous mixing. The resulting solution was smooth, nearly opaque, and viscous. The solution was characterized as anisotropic, or liquid crystalline, on the basis of its rheology, overall appearance, and optical properties.

The solution was loaded into a syringe having a four-screen filter pack consisting, in order, of 50, 325, 325, and 50 mesh screens in its top. The syringe was capped and centrifuged to disengage any air bubbles trapped in the solution. A syringe pump was then used to force the solution out of the syringe through a 0.005 inch (0.013 cm) diameter×0.020 inch (0.051 cm) length orifice in a stainless steel spinneret and directly into a jar of acetone at room temperature. The syringe pump speed was set to deliver solution at 0.0034 ml/min. The filament which formed as the solution was extruded into the acetone was allowed to fall freely and to coil on itself at the bottom of the jar.

After 64 hours of coagulation in the acetone, the filament was removed and allowed to dry in air at room temperature to produce a 36 denier (40 dtex) fiber having a tenacity of 0.82 gpd (0.72 dN/tex), an elongation of 177%, and an initial modulus of 25 gpd (22 dN/tex).

The dried filament was then drawn to 3×its original length while passing over a 215° C. hot pin to produce a 12 denier (13 dtex) fiber having a tenacity of 2.2 gpd (1.9 dN/tex), an elongation of 14%, and an initial modulus of 45 gpd (39.7 dN/tex).

Alternatively, fiber properties were improved by drawing the still-wet filament to 2×its original length before drying in air at room temperature temperature. The wet drawing produced a 21 denier (23 dtex) fiber having a tenacity of 2.1 gpd (1.9 dN/tex), an elongation of 37%, and an initial modulus of 32 gpd (28.3 dN/tex).

EXAMPLE 13

A 15.3% solution of silk fibroin isolated from the cocoons of the Chinese silkworm, Bombyx mori, in a solvent mixture of 90% formic acid and 10% lithium chloride was prepared by adding the mixed solvent to the dry polypeptide in a heat-sealed plastic packet, mixing thoroughly, and allowing the mixture to stand overnight at room temperature with intermittent additional mixing.

The solution was loaded into a syringe having a four-screen filter pack consisting, in order, of 50, 325, 325, and 50 mesh screens in its tip. The syringe was capped and centrifuged to disengage any air bubbles trapped in the solution. A syringe pump was then used to force the solution out of the syringe through a 0.005 inch (0.013 cm) diameter×0.010 inch (0.025 cm) length orifice in a stainless steel spinneret and directly into a jar of methanol at room temperature. The syringe pump speed was set to deliver solution at 0.034 ml/min. The filament which formed as the solution was extruded into the methanol was allowed to fall freely and to coil on itself at the bottom of the beaker.

After about 3 hours of coagulation in methanol, the filament was removed and allowed to dry in air at room temperature to produce a 125 denier (138 dtex) fiber having a tenacity of 0.4 gpd (0.35 dN/tex), an elongation of 1.2%, and an initial modulus of 36 gpd (32 dN/tex).

Alternatively, fiber properties were improved by drawing the still-wet filament to 4×its original length. The ends of the drawn filament were held fixed in order to prevent shrinkage during drying in air at room temperature to produce a 20 denier (22 dtex) fiber having a tenacity of 1.6 gpd, (1.4 dN/tex), an elongation of 10%, and an initial modulus of 61 gpd (54 dN/tex).

TABLE I

| Amino Acid | One-Letter Symbol |
|---|---|
| Alanine | A |
| Arginine | R |
| Asparagine | N |
| Aspartic Acid | D |
| Asparagine and/or Asparatic Acid | B |
| Cysteine | C |
| Glutamine | Q |
| Glutamic Acid | E |
| Glutamine and/or Glutamic Acid | Z |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |
| N-formylmethionine | fM |

I claim:
1. A process for forming polypeptide fibers, comprising the steps of:
   a) forming a spinnable solution comprising 5% to 30% by weight of a polypeptide, in a solvent, selected from the group consisting of hexafluoroisopropanol, and a mixture of formic acid and at least one lithium halide, and
   b) extruding the solution through a spinneret.
2. The process of claim 1, wherein the solution is extruded directly into a liquid coagulating medium to remove the solvent.
3. The process of claim 1, wherein the solution is extruded into an inert, non-coagulating fluid and then into a liquid coagulating medium to remove the solvent.
4. The process of claim 2 or 3, wherein the liquid coagulating medium comprises methanol.
5. The process of claim 1, wherein the solution is extruded into an inert gas to remove the solvent.
6. The process of claim 1, claim 2, claim 3, or claim 5, wherein the polypeptide consists essentially of multiple repetitive units of 5 to 150 amino acids, wherein each unit consists essentially of multiple repetitive sub-units of 3 to 30 amino acids, having sequences which confer some specific mechanical, chemical, or biological properties.

7. The process of claim 1, claim 2, claim 3, or claim 5, wherein the solution is liquid crystalline.

8. The process of claim 1, claim 2, claim 3, or claim 5, wherein the polypeptide consists essentially of multiple repetitive units of 5 to 150 amino acids, wherein each unit consists essentially of multiple repetitive sub-units of 3 to 30 amino acids, having sequences which confer some specific mechanical, chemical, or biological properties: and the solution is liquid crystalline.

9. The process of claim 4, wherein the polypeptide consists essentially of multiple repetitive units of 5 to 150 amino acids, wherein each unit consists essentially of multiple repetitive sub-units of 3 to 30 amino acids, having sequences which confer some specific mechanical, chemical, or biological properties.

10. The process of claim 4, wherein the solution is liquid crystalline.

11. The process of claim 4, wherein the polypeptide consists essentially of multiple repetitive units of 5 to 150 amino acids, wherein each unit consists essentially of multiple repetitive sub-units of 3 to 30 amino acids, having sequences which confer some specific mechanical, chemical, or biological properties; and the solution is liquid crystalline.

12. A process for forming polypeptide fibers, comprising the steps of:
a) forming a spinnable solution comprising 5% to 30% by weight of a polypeptide, urea, and hexafluoroiso*propanol; and
b) extruding the solution through a spinneret.

13. A process for forming polypeptide fibers comprising the steps of:
a) forming a spinnable solution comprising 5% to 30% by weight of a polypeptide, in a solvent, selected from the group consisting of hexafluoroisopropanol, a mixture of formic acid and lithium chloride, and a mixture of formic acid and lithium bromide; and
b) extruding the solution through a spinneret.

14. The process of claim 3, wherein the inert, non-coagulating fluid is air.

15. The process of claim 2 or 3, further comprising the steps of:
c) drying the polypeptide fibers, and
d) drawing the fibers.

16. The process of claim 2 or 3, further comprising the steps of:
c) drawing the polypeptide fibers, while the fibers are wet with coagulating fluid.

17. The process of claim 16, further comprising the step of:
d) drying the fibers under tension.

* * * * *